(12) United States Patent
Miki et al.

(10) Patent No.: US 8,268,876 B2
(45) Date of Patent: *Sep. 18, 2012

(54) PHARMACEUTICAL COMPOSITION FOR EXTERNAL USE

(75) Inventors: Toyohiko Miki, Yokohama (JP); Akira Nozawa, Yokohama (JP); Nobuo Kubota, Yokohama (JP); Susumu Tomiyama, Yokohama (JP); Hirokazu Kobayashi, Yokohama (JP)

(73) Assignees: Nihon Nohyaku Co., Ltd., Chuo-ku, Tokyo (JP); Pola Pharma Inc., Shinagawa-ku, Tokyo (JP)

( * ) Notice: Subject to any disclaimer, the term of this patent is extended or adjusted under 35 U.S.C. 154(b) by 137 days.

This patent is subject to a terminal disclaimer.

(21) Appl. No.: 12/281,969

(22) PCT Filed: Oct. 2, 2006

(86) PCT No.: PCT/JP2006/319705
§ 371 (c)(1),
(2), (4) Date: Sep. 5, 2008

(87) PCT Pub. No.: WO2007/102241
PCT Pub. Date: Sep. 13, 2007

(65) Prior Publication Data
US 2009/0030059 A1   Jan. 29, 2009

(30) Foreign Application Priority Data

Mar. 8, 2006 (JP) ................ 2006-062078
Aug. 8, 2006 (JP) ................ 2006-215904

(51) Int. Cl.
*A61K 31/415* (2006.01)
(52) U.S. Cl. ..................................... 514/397
(58) Field of Classification Search ........... None
See application file for complete search history.

(56) References Cited

U.S. PATENT DOCUMENTS

| | | |
|---|---|---|
| 4,267,169 A | 5/1981 | Kamishita et al. |
| 4,636,520 A | 1/1987 | Umio et al. |
| 4,764,381 A | 8/1988 | Bodor et al. |
| 5,340,836 A | 8/1994 | Reinhard et al. |
| 5,690,923 A | 11/1997 | De Vringer et al. |
| 5,753,256 A | 5/1998 | Cordes et al. |
| 5,962,536 A | 10/1999 | Komer |
| 5,993,787 A | 11/1999 | Sun et al. |
| 6,007,791 A | 12/1999 | Coombes et al. |
| 6,008,256 A | 12/1999 | Haraguchi et al. |
| 6,017,920 A | 1/2000 | Kamishita et al. |
| 6,083,518 A | 7/2000 | Lindahl |
| 6,428,654 B1 | 8/2002 | Cronan, Jr. et al. |
| 6,585,963 B1 | 7/2003 | Quan et al. |
| 6,740,326 B1 | 5/2004 | Meyer et al. |
| 2003/0017207 A1 | 1/2003 | Lin et al. |
| 2003/0235541 A1 | 12/2003 | Maibach et al. |
| 2004/0208906 A1 | 10/2004 | Tatara et al. |
| 2005/0232879 A1 | 10/2005 | Sasagawa et al. |
| 2006/0140984 A1 | 6/2006 | Tamarkin et al. |
| 2007/0099932 A1 | 5/2007 | Shirouzu et al. |
| 2008/0031835 A1 | 2/2008 | Kawamura et al. |
| 2009/0030059 A1 | 1/2009 | Miki et al. |
| 2009/0076109 A1 | 3/2009 | Miki et al. |
| 2009/0099202 A1 | 4/2009 | Shirouzu et al. |
| 2009/0137651 A1 | 5/2009 | Kobayashi et al. |
| 2009/0202602 A1 | 8/2009 | Ishima et al. |
| 2010/0168200 A1 | 7/2010 | Masuda et al. |
| 2010/0173965 A1 | 7/2010 | Masuda et al. |
| 2010/0204293 A1 | 8/2010 | Masuda et al. |
| 2010/0210702 A1 | 8/2010 | Vontz et al. |
| 2010/0210703 A1 | 8/2010 | Vontz et al. |

FOREIGN PATENT DOCUMENTS

| | | |
|---|---|---|
| EP | 0 070 525 | 1/1983 |
| EP | 0 440 298 | 8/1991 |
| EP | 0 715 856 | 6/1996 |
| EP | 1 138 314 | 10/2001 |
| EP | 1 522 316 | 4/2005 |
| EP | 1 537 868 | 6/2005 |
| EP | 1 637 132 | 3/2006 |
| EP | 2 005 958 | 12/2008 |
| EP | 2 005 959 | 12/2008 |
| EP | 2 025 337 | 2/2009 |
| EP | 2 191 827 | 6/2010 |
| JP | 61-118315 | 6/1986 |
| JP | 62-093227 | 4/1987 |

(Continued)

OTHER PUBLICATIONS

Niwano et al (Int J Antimicrobial Agents 12:221-228, 1999).*
Uchida et al (J Infect Chemother 10:216-219, 2004).*
Costa Martins et al (Clinics 61(1):9-14, 2006).*
www.babymd.com (available online as of Feb. 16, 2001 as evidenced by the attached Internet Archive report) accessed online Dec. 18, 2010.*
Examination Report issued Apr. 8, 2010 to corresponding New Zealand Patent Application No. 571818.
Supplementary European Search Report mailed Aug. 16, 2010 and issued to European application No. 06811056.8-2123/2005958.
Uchida, et al. "In vitro Antifungal Activity of Luliconazole (NND-502), a Novel Imidazole Antifungal Agent," *J Infect Chemother*, vol. 10, pp. 216-219, 2004.

(Continued)

*Primary Examiner* — Craig Ricci
(74) *Attorney, Agent, or Firm* — Knobbe, Martens, Olson & Bear, LLP (57) ABSTRACT

Provided is a pharmaceutical composition for external use, including: (i) luliconazole represented by the following structural formula (1) and/or a salt thereof; and (ii) α-hydroxycarboxylic acid and/or a salt thereof.

Structural formula (1)

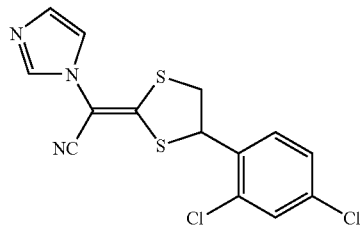

4 Claims, 6 Drawing Sheets

FOREIGN PATENT DOCUMENTS

| | | |
|---|---|---|
| JP | 62-223163 | 10/1987 |
| JP | 01-242525 | 9/1989 |
| JP | 01-246219 | 10/1989 |
| JP | 02-264723 | 10/1990 |
| JP | 02-275877 | 11/1990 |
| JP | 05-306223 | 11/1993 |
| JP | 06-199701 | 7/1994 |
| JP | 06-211651 | 8/1994 |
| JP | 07-188027 | 7/1995 |
| JP | 07-74144 | 8/1995 |
| JP | 07-206711 | 8/1995 |
| JP | 07-223971 | 8/1995 |
| JP | 08-020527 | 1/1996 |
| JP | 10-152433 | 6/1998 |
| JP | 10-226639 | 8/1998 |
| JP | 10-226686 | 8/1998 |
| JP | 2001-064206 | 3/2001 |
| JP | 2002-114680 | 4/2002 |
| JP | 2002-193755 | 7/2002 |
| JP | 2002-284702 | 10/2002 |
| JP | 2002-363070 | 12/2002 |
| JP | 2003-252798 | 9/2003 |
| JP | 2004-529923 | 9/2004 |
| JP | 2005-154306 | 6/2005 |
| JP | 2005-239678 | 9/2005 |
| JP | 2005-289879 | 10/2005 |
| JP | 2006-028123 | 2/2006 |
| JP | 2006-306734 | 11/2006 |
| RU | 2 270 894 C2 | 3/2004 |
| WO | WO 90/14094 | 11/1990 |
| WO | WO 95/30440 | 11/1995 |
| WO | WO 96/11710 | 4/1996 |
| WO | WO 96/40047 | 12/1996 |
| WO | WO 97/02821 | 1/1997 |
| WO | WO 97/07794 | 3/1997 |
| WO | WO 00/01384 | 1/2000 |
| WO | WO 02/062336 * | 8/2002 |
| WO | WO 02/083084 | 10/2002 |
| WO | WO 02/087570 | 11/2002 |
| WO | WO 03/020248 | 3/2003 |
| WO | WO 03/105841 | 12/2003 |
| WO | WO 2004/021968 | 3/2004 |
| WO | WO 2004/084826 | 10/2004 |
| WO | WO 2004/091521 | 10/2004 |
| WO | WO 2006/038317 | 4/2005 |
| WO | WO 2005/099764 | 10/2005 |
| WO | WO 2005/123136 | 12/2005 |
| WO | WO 2007/102242 | 9/2007 |
| WO | WO 2007/077806 | 12/2007 |
| WO | WO 2008/075207 | 6/2008 |
| WO | WO 2010/093992 | 8/2010 |

OTHER PUBLICATIONS

Uchida, et al. "In vitro Activity of Novel Imidazole Antifungal Agent NND-502 Against *Malassezia* Species," *International Journal of Antimicrobial Agents*, vol. 21, pp. 234-238, 2003.

Supplemental European Search Report dated Aug. 10, 2010, issued to corresponding European patent application 06811053.5.

Borrás-Blasco, et al. "A Mathematical Approach to Predicting the Percutaneous Absorption Enhancing Effect of Sodium Lauryl Sulphate," *International Journal of Pharmaceutics*, vol. 269, pp. 121-129, 2004.

International Search Rep[ort dated Nov. 18, 2008 issued to international application No. PCT/JP2008/066058.

International Search Report dated Nov. 18, 2008 issued to international application No. PCT/JP2008/066057.

International Search Report dated Nov. 18, 2008 issued to international application No. PCT/JP2008/066056.

Office action issued to related Israeli Patent Application No. 193894 on Oct. 14, 2010 with translation.

Supplementary European Search Report issued Aug. 12, 2010 to related European application No. 08829061.4.

Supplementary European Search Report issued Aug. 12, 2010 to related European application No. 08829224.8.

Niwano, et al. "In vitro and In vivo Antidermatophyte Activities of NND-4502, a Novel Optically Active Imidazole Antimycotic Agent," *Antimicrobial Agents and Chemotherapy*, vol. 42, No. 4, pp. 967-970, Apr. 1998.

GHS Classification Guidance for Enterprises (2nd Edition, Ministry of Economy, Trade and Industry, Japan, Mar. 2010.

Crotamiton Properties (http://www.chemspider.com/Chemical-Structure.2780.html) 2 pages.

Absolute ethanol MSDS (www.sciencelab.com/msds.php?msdsld=9923955) 7 pages.

Methyl Ethyl Ketone MSDS (www.sciencelab.com/msds.php?msdsld=9927358) 6 pages.

Niwano, et al. "Lanoconazole and Its Related Optically Active Compound NND-502: Novel Antifungal Imidazoles with a Ketene Dithioacetal Structure," *Current Medicinal Chemistry*, vol. 2, pp. 147-160, 2003.

\* cited by examiner

PHARMACEUTICAL COMPOSITION FOR EXTERNAL USE

CROSS-REFERENCE TO RELATED APPLICATIONS

This application is the U.S. National Phase under 35 U.S.C. §371 of International Application PCT/JP2006/319705, filed Oct. 2, 2006, which was published in a non-English language, which claims priority to JP Patent Application No. 2006-062078, filed Mar. 8, 2006 and JP Patent Application No. 2006-215904, filed Aug. 8, 2006.

TECHNICAL FIELD

The present invention relates to a pharmaceutical composition for external use, and more particularly, to a pharmaceutical composition for external use for treatment or prevention of onychomycosis or hyperkeratotic trichophytosis.

BACKGROUND ART

The Japanese archipelago extends from a subtropical zone to a temperate zone and has a warm climate high in humidity, which is liable to facilitate propagation of fungi such as molds. In addition, due to westernization of clothes, people are now accustomed to wearing shoes on feet. Accordingly, a foot serves as a favorable environment for the propagation of the fungi, leading to mycotic skin diseases that are serious social issues nowadays. Of those, onychomycosis has a low complete cure rate and high relapsing and reinfection rates. Therefore, an effective therapy has been demanded.

Conventionally, treatments mainly using tolnaftate formulations have been conducted on such diseases. In recent years, imidazole-based antifungal agents, such as bifonazole and itraconazole, are mainly used.

As the imidazole-based antifungal agents, there are commercially available imidazole-based antifungal agents such as those represented by the general formula (1) described below, specifically, luliconazole represented by the structural formula (1) below and lanoconazole represented by the structural formula (2) below. The above-mentioned luliconazole is currently the newest imidazole-based antifungal agent, and a commercially available product called "Lulicon" (registered trademark) is also present (e.g., see Patent Document 1 and Patent Document 2).

The luliconazole is an imidazole-based antifungal agent having optical activity, and has a wide antifungal spectrum, in particular, remarkable antifungal activity against dermatophytes. In addition, the luliconazole is also characterized by having extremely high retention property in the stratum corneum, and is a composition thus expected for application to the treatment of onychomycosis. However, nail acts as barrier to penetration of external materials including chemical substances, antifungal agents hardly reaches a region where the pathogenic fungi are present. Therefore, the above-mentioned luliconazole alone is insufficient to exert effects on the onychomycosis.

On the otherhand, asmeans foracceleratingpercutaneous absorption of a material having antifungal activity, such as the above-mentioned luliconazol, benzyl alcohol has been known to be used as a penetration accelerator.

Further, in the field of antifungal agents, in addition to the above-mentioned benzyl alcohol, means for facilitating the agent to proceed into the nail have been known in the art, including: a method of combining materials for softening the nail, such as urea and salicylic acid (e.g., see Patent Document 3 and Patent Document 4); a method using fatty acid ester (e.g., see Patent Document 5 and Patent Document 6); and a method of utilizing absorption-promoting agents, such as higher alcohol, organic base, dimethylformamide (DMF), and dimethyl sulfoxide (DMSO). However, in any of the cases, the effects were not sufficient.

Further, as an attempt to treat onychomycosis by means of a compound represented by the general formula 1 below, a method of forming a reservoir layer by combining a film-forming agent with a polyoxypropylene/polyoxyethylene copolymer (e.g., see Patent Document 9) has been developed, resulting in significant improvement in effect thereof. However, when the nail becomes hard after recovering from the onychomycosis to some extent, there is a disadvantage in that a decrease in effect occurs.

General formula (1)

[Chem 1]

(where X represents a hydrogen atom or a chloride atom)

Structural formula (1)

[Chem 2]

Structural formula (2)

[Chem 3]

Patent Document 1: JP 62-93227 A
Patent Document 2: JP 10-226686 A
Patent Document 3: JP 10-152433 A
Patent Document 4: JP 10-226639 A
Patent Document 5: JP 07-206711 A
Patent Document 6: WO 96/11710
Patent Document 7: JP 06-211651 A Patent Document 8: JP 2004-529923 A
Patent Document 9: WO 03/105841

DISCLOSURE OF THE INVENTION

Problem to be Solved by the Invention

As described above, it is known that a material having antifungal activity, such as luliconazole, has difficulty in percutaneous absorption, and that benzyl alcohol or the like is used as a penetration accelerator as means for accelerating the percutaneous absorption. However, the present inventors have found that in the above-mentioned luliconazole, the benzyl alcohol or the like does not exert a sufficient effect of accelerating the penetration.

The present invention has been made based on the above-mentioned finding, and therefore has an object to provide a pharmaceutical composition for external use having excellent penetration and absorption properties by finding out a factor that inhibits the penetration and absorption properties of the pharmaceutical composition for external use containing luliconazole and/or a salt thereof, and developing means for eliminating the inhibitory factor.

Means for Solving the Problems

In consideration of the above-mentioned circumstances, as a result of intensive studies for finding out a factor that inhibits the penetration-absorption of luliconazole and/or a salt thereof into a living body, the present inventors have found that a fine crystal of luliconazole is instantaneously precipitated when a pharmaceutical preparation containing as effective components luliconazole and/or a salt thereof is applied onto the living body, and that the precipitation of the crystal inhibits the penetration-absorption. Further, as a result of further intensive studies, the present inventors have found that the precipitation of the crystal can be suppressed by an addition of α-hydroxycarboxylic acid and/or a salt thereof, such as lactic acid, thereby completing the present invention. In other words, the present invention is as follows.

(1) A pharmaceutical composition for external use, including:
(i) luliconazole represented by the following structural formula (1) and/or a salt thereof; and
(ii) α-hydroxycarboxylic acid and/or a salt thereof.

Structural formula (1)

[Chem 4]

(2) A pharmaceutical composition for external use according to the above-mentioned item (1), in which the α-hydroxycarboxylic acid is lactic acid, glycolic acid, or malic acid.

(3) A pharmaceutical composition for external use according to the above-mentioned item (1) or (2), in which the α-hydroxycarboxylic acid is lactic acid.

(4) A pharmaceutical composition for external use according to the above-mentioned item (1), further including benzyl alcohol.

(5) A pharmaceutical composition for external use according to the above-mentioned item (1), further including diester of dibasic acid.

(6) A pharmaceutical composition for external use according to the above-mentioned item (5), in which the diester of dibasic acid is a diester of dibasic acid and alcohol having 1 to 4 carbon atoms.

(7) A pharmaceutical composition for external use according to the above-mentioned item (5), in which the diester of dibasic acid is a diethyl ester or diisopropyl ester of adipic acid or sebacic acid.

(8) A pharmaceutical composition for external use according to the above-mentioned item (1), further including N-methyl-2-pyrrolidone.

(9) A pharmaceutical composition for external use according to the above-mentioned item (1) to, which is provided for treatment or prevention of onychomycosis.

(10) A pharmaceutical composition for external use according to above-mentioned item (1), which is provided for treatment or prevention of horny-outgrowing type hyperkeratotic trichophytosis.

Effects of the Invention

According to the present invention, it is possible to develop means for suppressing a factor that inhibits the acceleration of the penetration-absorption in an external preparation containing a compound represented by the general formula 1 and/or a salt thereof so as to provide an antifungal pharmaceutical composition excellent in penetration-absorption.

BEST MODE FOR CARRYING OUT THE INVENTION (1) Luliconazole and/or a Salt Thereof as Essential Components of a Pharmaceutical Composition for External Use (Hereinafter, Referred to as Pharmaceutical Composition of the Present Invention)

The pharmaceutical composition for external use according to the present invention contains as essential components luliconazole and/or a salt thereof (hereinafter, also referred to as luliconazole or the like). The above-mentioned luliconazole is represented by the above-mentioned structural formula (1). The above-mentioned luliconazole is a known compound represented by (R)-(−)-(E)-[4-(2,4-dichlorophenyl)-1,3-dithiolan-2-iliden]-1-imidazolyl acetonitrile. Its manufacturing method and the antifungal properties are already known in the art. JP 62-93227 A (Patent Document 1 above) can be used as reference.

In addition, "salt thereof" is not specifically limited as far as it is physiologically acceptable. Preferable examples thereof include: mineral acid salts such as hydrochloride, nitrate, sulfate, and phosphate; organic acid salts such as citrate, oxalate, lactate, and acetate; and sulfuric acid-containing salts such as mesilate and tosilate. In terms of safety and solubility, hydrochloride is more preferable.

In the pharmaceutical composition for external use according to the present invention, the content of luliconazole or the like is preferably 0.1 to 30% by mass, more preferably 0.5 to 15% by mass in total with respect to the total amount of the pharmaceutical composition. The content of luliconazole or the like can be determined based on its solubility and formulation characteristics.

(2) α-Hydroxycarboxylic Acid and/or a Salt Thereof Used in Pharmaceutical Composition for External Use According to the Present Invention The pharmaceutical composition for external use according to the present invention contains α-hydroxycarboxylic acid and/or a salt thereof (hereinafter, also referred to as α-hydroxycarboxylic acid or the like) as an essential component. The α-hydroxycarboxylic acid may be, for example, any of α-hydroxycarboxylic acids having 2 to 5 carbon atoms. Of those, lactic acid, glycolic acid, and malic acid can be preferably exemplified. In particular, of those, lactic acid is preferable. Further, those salts are not specifically limited as far as they can be used for pharmaceutical preparations and are physiologically acceptable. Preferable examples thereof include: alkali metal salts, such as sodium salt and potassium salt; alkaline earth metal salts, such as calcium salt and magnesium salt; organic amine salts, such as ammonium salt, triethylamine salt, and triethanol amine salt; and basic amino acid salts, such as arginine salt and lysine salt. The pharmaceutical composition for external use according to the present invention can contain only one kind of those components or two or more in combination.

In the pharmaceutical composition for external use according to the present invention, when applied, the component acts to suppress crystallization and precipitation of luliconazole or the like on the applied surface. Such an insoluble matter such as crystal or precipitation suppressing action allows luliconazole or the like to be absorbed into the body without any interruption. Therefore, the penetration-promoting agent, such as the benzyl alcohol, can fully exert its function.

Such an action cannot be sufficiently attained with acids other than α-hydroxycarboxylic acids. For exerting such an action, the content of α-hydroxycarboxylic acid in the pharmaceutical composition for external use according to the present invention is 0.1 to 20% by mass, preferably 1 to 10% by mass in total with respect to the total amount of the pharmaceutical composition. This is because the above-mentioned action may not be exerted if it is too low, and the effect reaches the limit and may restrict the mixing amounts of other components if it is too high.

Further, for exerting the insoluble matter such as crystal or precipitation suppressing action of luliconazole or the like by the α-hydroxycarboxylic acid or the like, the mass ratio of α-hydroxycarboxylic acid or the like to luliconazole or the like (i.e., α-hydroxycarboxylic acid or the like/luliconazole or the like) is preferably 0.1 to 10, more preferably 0.5 to 5, particularly preferably 0.8 to 2.

(3) Benzyl Alcohol Used in Pharmaceutical Composition for External Use According to the Present Invention The pharmaceutical composition for external use according to the present invention preferably contains benzyl alcohol. The benzyl alcohol is already used as an additive in pharmaceutical compositions and is commercially available, so it can be obtained with ease. In the presence of the α-hydroxycarboxylic acid or the like, the benzyl alcohol exerts actions of suppressing precipitation of crystals of luliconazole or the like on a living body upon application to also suppress inhibition of the penetration thereof into the living tissue, particularly into the nail. Therefore, the combination of benzyl alcohol with α-hydroxycarboxylic acid synergistically improves the orientation of agents to the nail matrix. For exerting such an action, the content of benzyl alcohol is preferably 0.5 to 15% by mass, particularly preferably 1 to 10% by mass with respect to the total amount of the pharmaceutical composition. In other words, if the content of benzyl alcohol is outside the above-mentioned range, luliconazole or the like may be crystallized and precipitated at the time of application. Therefore, as the crystallization and precipitation are suppressed at the time of application, the benzyl alcohol fully exerts its original effect of accelerating tissue penetration.

(4) Diester of Dibasic Acid Used in Pharmaceutical Composition for External Use According to the Present Invention The pharmaceutical composition for external use according to the present invention preferably contains a diester of dibasic acid, in particular, any of diesters of dibasic acids and alcohols having 1 to 4 carbon atoms. Examples of the dibasic acids include those having 1 to 10 carbon atoms, preferably, adipic acid, sebacic acid, oxalic acid, and carbonic acid. On the other hand, preferable examples of the alcohols having 1 to 4 carbon atoms include methyl alcohol, ethyl alcohol, propyl alcohol, isopropyl alcohol, butyl alcohol, isobutyl alcohol, and tert-butyl alcohol. Alternatively, any of polyalcohols, such as ethylene glycol and propylene glycol may be used as the alcohol having 1 to 4 carbon atoms.

Specifically, preferable examples of diesters of the above-mentioned dibasic acids include propylene carbonate, diethyl adipate, diisopropyl adipate, diethyl sebacate, and diisopropyl sebacate. Of those, diisopropyl adipate and diethyl sebacate are particularly preferable. The pharmaceutical composition for external use according to the present invention can contain a single kind of those components or two or more in combination. In the presence of the α-hydroxycarboxylic acid or the like, the component, together with the benzyl alcohol and N-methyl-2-pyrrolidone described later, exerts its actions of promoting penetration of luliconazole or the like into the living tissue, particularly into the nail. For exerting such an action, in the pharmaceutical composition for external use according to the present invention, the content of the component is preferably 1 to 30% by mass, more preferably 5 to 15% by mass in total with respect to the total amount of the pharmaceutical composition.

(5) N-methyl-2-pyrrolidone Used in Pharmaceutical Composition for External Use According to the Present Invention The pharmaceutical composition for external use according to the present invention preferably contains N-methyl-2-pyrrolidone.

The N-methyl-2-pyrrolidone is already used as an additive in pharmaceutical compositions and is commercially available, so it can be obtained with ease. In the presence of the α-hydroxycarboxylic acid or the like, N-methyl-2-pyrrolidone, together with the benzyl alcohol, diester of dibasic acid, or the like, exerts its actions of promoting penetration of luliconazole or the like into the living tissue, particularly into the nail. For exerting such an action, in the pharmaceutical composition for external use according to the present invention, the content of the component is preferably 1 to 15% by mass, particularly preferably 3 to 10% by mass with respect to the total amount of the pharmaceutical composition. N-methyl-2-pyrrolidone also has a function of preventing luliconazole from being transformed into an isomeric form during storage.

(6) Pharmaceutical Composition for External Use According to the Present Invention In the pharmaceutical composition for external use according to the present invention, benzyl alcohol, diester of dibasic acid, and N-methyl-2-pyrrolidone exert their respective synergetic effects on the pharmaceutical composition for external use containing luliconazole or the like and α-hydroxylic acid or the like, so any one of those may be used in combination. However, they have their own mechanisms to accelerate the penetration of the pharmaceutical composition for external use containing luliconazole or the like and α-hydroxylic acid or the like into the nail, so it is preferable that those compounds be used in a form of containing at least benzyl alcohol, more preferably a combination of two or more in the form of containing at least benzyl alcohol, particularly preferably in the form of containing benzyl alcohol, diester of dibasic acid, and N-methyl-2-pyrrolidone. This is because the benzyl alcohol provides the pharmaceutical composition for external use containing luliconazole or the like and α-hydroxylic acid or the like with a significant synergetic effect (penetration-accelerating effect). Further, N-methyl-2-pyrrolidone also has a function of preventing luliconazole or the like from being transformed into an isomeric form during storage as well as a penetration-accelerating effect, and the stability of the above-mentioned pharmaceutical composition over time can be thus improved.

The pharmaceutical composition for external use according to the present invention can contain any of components commonly used in pharmaceutical compositions in addition to those described above, as far as it does not impair the effects according to the present invention.

Preferable examples of such components include: hydrocarbons such as vaseline and microcrystalline wax; esters such as jojoba oil, cetaceum, triacetin, triethyl citrate, and butyl acetate; triglycerides such as beef tallow and olive oil; higher alcohols such as cetanol and oleyl alcohol; fatty acids such as stearic acid and oleic acid; alcohols such as ethanol and isopropanol; polyalcohols such as glycerin and 1,3-butanediol; water; non-ionic surfactants; anionic surfactants; cationic surfactants; amphoteric surfactants; thickeners such as polyvinyl pyrrolidone and carbopol; preservatives; UV absorbers; antioxidants; pigments; and powders. Those optional components and the above-mentioned component are treated by common procedures, whereby a pharmaceutical composition for external use according to the present invention can be produced. The pharmaceutical composition for external use according to the present invention is not specifically limited as far as it is formulated into any of forms used for pharmaceutical compositions for external use, and preferable examples thereof include lotions, emulsions, gelatinizing agents, cream pharmaceuticals, aerosols, nail enamel agents, and hide gel patches. Of those, the lotions are most preferable. For stabilizing the clarity and color of solution such as luliconazole, 50 to 90% by mass of ethanol is most preferably contained.

The pharmaceutical composition for external use according to the present invention is preferably used for treating mycotic diseases or preventing progression of the diseases by using characteristics of luliconazole or the like. The mycotic diseases include: foot trichophytosis such as athlete's foot; trichophytosis corporis such as candida and pityriasis versicolor; and trichophytosis on a hard keratin portion, such as onychomycosis. Because of remarkable effects, it is particularly preferable to use the pharmaceutical composition for external use according to the present invention for treating the hard keratin portion, such as onychomycosis. In particular, the pharmaceutical composition for external use according to the present invention exerts preferable effects on the nail and such an effect is also exerted on typical dermatomycosis. Therefore, the application of a pharmaceutical composition for external use against dermatomycosis, which satisfies the configuration according to the present invention, is also within the technical scope according to the present invention. Examples of such dermatomycosis include trichophytosis such as foot trichophytosis, particularly horny-outgrowing type hyperkeratotic trichophytosis which appears on heels or the like. The present invention has a significant effect on the horny-outgrowing type hyperkeratotic trichophytosis, on which the conventional agents hardly exert their effects, among the above-mentioned dermatomycosis, which is preferable.

With regard to its use, for example, the pharmaceutical composition is applied on a diseased portion one or several times a day and the treatment is preferably carried out day after day. In particular, for onychomycosis, luliconazole or the like, which is an effective component in an amount that cannot be attained by normal formulation, can be transferred into the nail. Therefore, onychomycosis can be treated only by the external application without having to drink an anti-fungal agent over a long period of time. In addition, recurrence and reinfection have been a major problem for onychomycosis. However, the recurrence and reinfection can be prevented by administration of the pharmaceutical composition for external use according to the present invention for 1 to 2 weeks after abatement of the symptom. Therefore, the pharmaceutical composition for external use according to the present invention exerts preventive efficacy in this aspect.

EXAMPLES

Hereinafter, the present invention will be described in more detail with reference to examples. However, the present invention is not limited to those examples.

Examples 1 to 3 and Comparative Examples 1 to 3

Lotions 1 to 3 containing the pharmaceutical compositions according to the present invention and Comparative Lotions 1 to 3 were prepared on the basis of the formulations shown in Table 1 below. That is, formulation components were dissolved by mixing at room temperature while stirring, thereby preparing each lotion. After the application of each lotion, the formulation-stabilizing action thereof was investigated. In other words, one drop of each of Lotions 1 to 3 and Comparative Lotions 1 to 3 was dropped on a slide glass and then air-dried for five minutes, followed by microscopic observation to determine the degree of insoluble matter such as crystal or precipitation.

TABLE 1

| Components | % by mass | | | | | |
|---|---|---|---|---|---|---|
| | Lotion 1 | Lotion 2 | Lotion 3 | Comparative Lotion 1 | Comparative Lotion 2 | Comparative Lotion 3 |
| Luliconazole | 1 | 3 | 5 | 1 | 3 | 5 |
| Lactic acid | 1 | 4 | 8 | — | — | — |
| Ethanol | 98 | 93 | 87 | 99 | 97 | 95 |
| Total | 100 | 100 | 100 | 100 | 100 | 100 |
| insoluble matter such as crystal or precipitation | N/A | N/A | N/A | Detected | Detected | Detected |

Example 4 and Comparative Examples 4 and 5

Lotion 4 containing the pharmaceutical compositions according to the present invention was prepared on the basis of the formulation shown in Table 2 below. That is, formulation components were dissolved by mixing at room temperature while stirring, thereby preparing Lotion 4.

TABLE 2

| Components | % by mass |
|---|---|
| Luliconazole | 5 |
| Benzyl alcohol | 2 |
| Lactic acid | 4 |
| Ethanol | 89 |
| Total | 100 |

Figure 1:
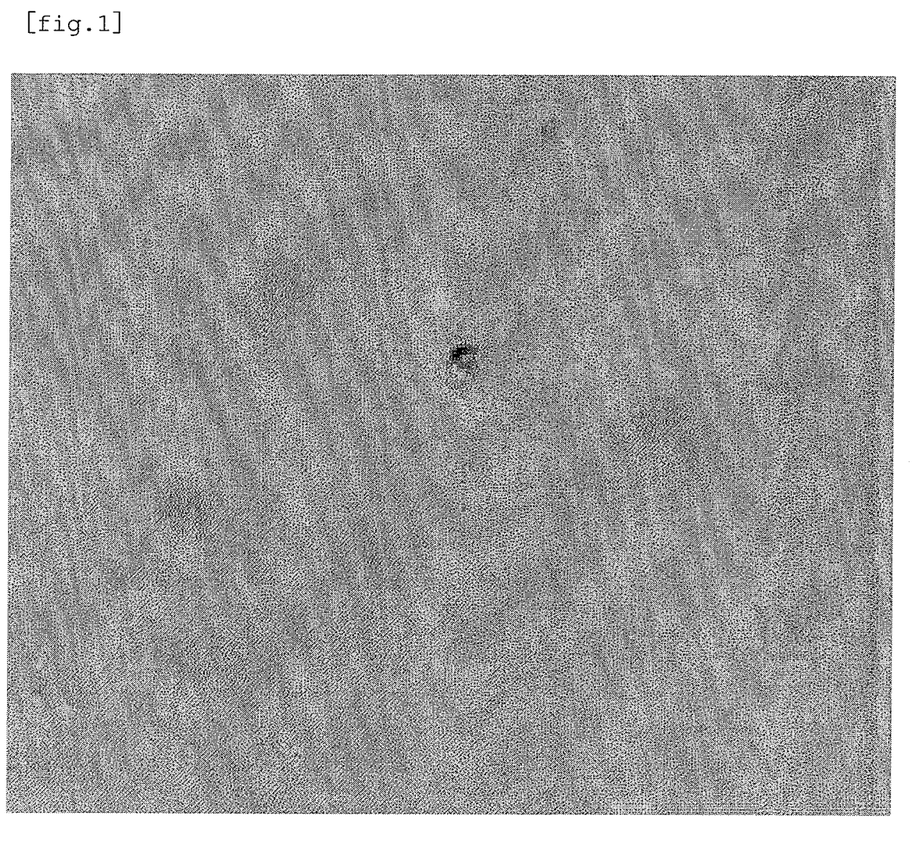
FIG. 1 is a microphotographic view of Lotion 4 of Example 4.
Figure 2:
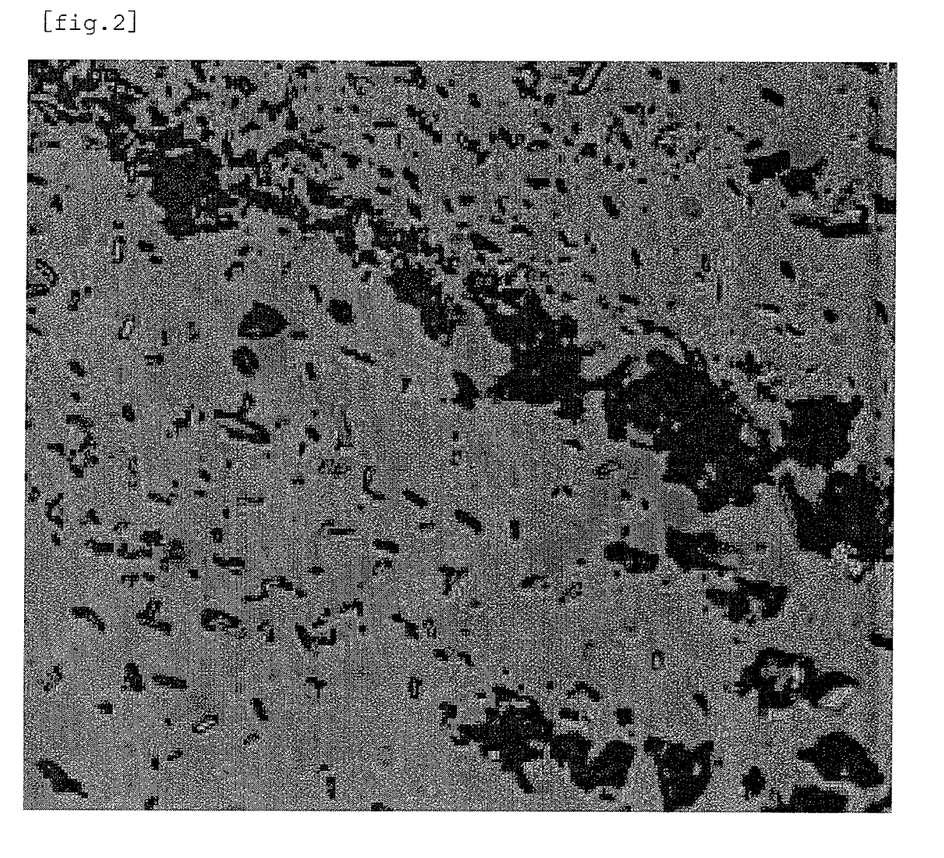
FIG. 2 is a microphotographic view of comparative Lotion 4 of Example 4.
Figure 3:
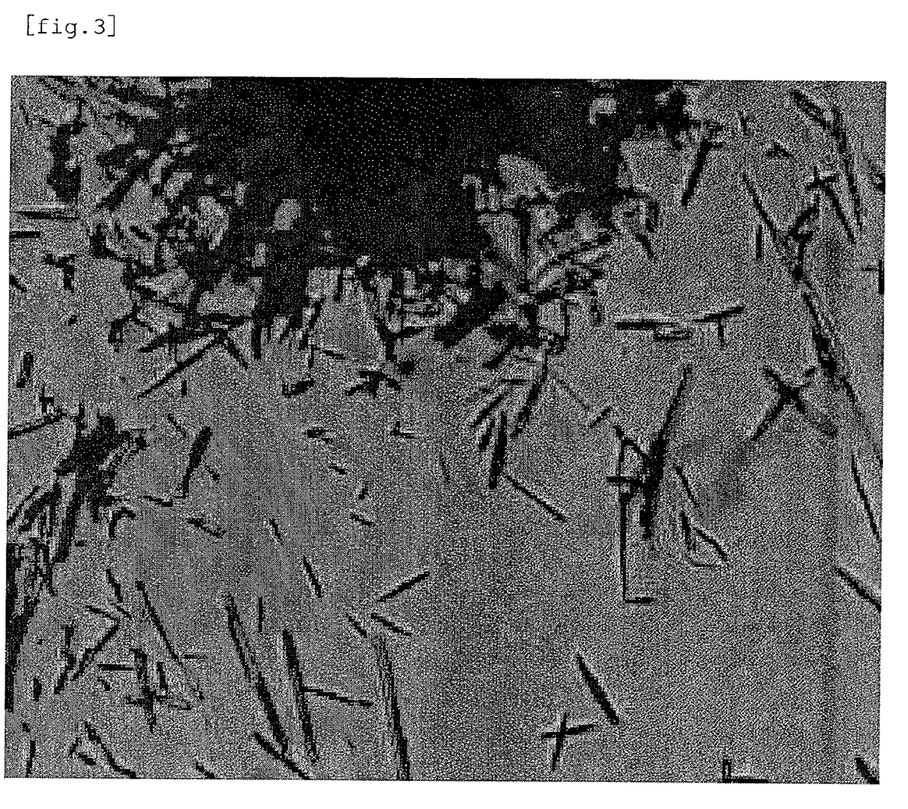
FIG. 3 is a microphotographic view of comparative Lotion 5 of Example 4.

In the formulation of Example 4, Comparative Lotion 4 (Comparative Example 4) in which lactic acid was replaced with ethanol and Comparative Lotion 5 (Comparative Example 5) in which lactic acid was replaced with phosphoric acid were prepared, respectively. Subsequently, those lotions as well as Lotion 4 were investigated for their formulation-stabilizing actions after application. In other words, one drop of each of Lotion 4, Comparative Lotion 4, and Comparative Lotion 5 was dropped on a slide glass and then air-dried for five minutes, followed by microscopic observation to determine the degree of insoluble matter such as crystal or precipitation. The degree of insoluble matter such as crystal or precipitation was calculated as an area ratio of a precipitated crystal to the area of one microscopic view field (means of three view fields). The results were 0% in Lotion 4, 11% in Comparative Lotion 4, and 9% in Comparative Lotion 5, respectively. FIGS. 1 to 3 show microscopic photographs of Lotion 4, Comparative Lotion 4, and Comparative Lotion 5, respectively. Accordingly, it is found that Lotion 4, which contains the pharmaceutical composition according to the present invention, is suppressed in its insoluble matter such as crystal or precipitation on the applied surface.

Further, for Lotion 4 and Comparative Lotion 4 described above, the amount of agent that has penetrated through the nail was measured. In other words, front and back sides of a piece of a human nail were sandwiched by polytetrafluoroethylene plates provided with O-shaped rings (2 mm in inner diameter), and the plates were then fixed on Franz cells (open-top cells, Central Riken K.K.), respectively. Agar was injected into the cell on the backside of the nail and then fixed, followed by applying 0.5 µL of the sample in the O-shaped ring on the cell on the front side of the nail. The application was performed once a day for three days. After 24 hours from the last application, the nail in the O-shaped ring was punched out and luliconazole was then extracted with methanol. The extract was determined for the amount of luliconazole in the nail by a high-performance liquid chromatographic method. Consequently, the amount of agent that has penetrated through the nail with respect to Comparative Lotion 4 was 0.60 when the amount of agent that has penetrated through the nail with respect to Lotion 4 was 1 (the amount of agent that has penetrated through the nail with respect to Lotion 4 was 1.67 when the amount of agent that has penetrated through the nail with respect to Comparative Lotion 4 was 1).

Example 5 and Comparative Examples 6 and 7

Figure 4:
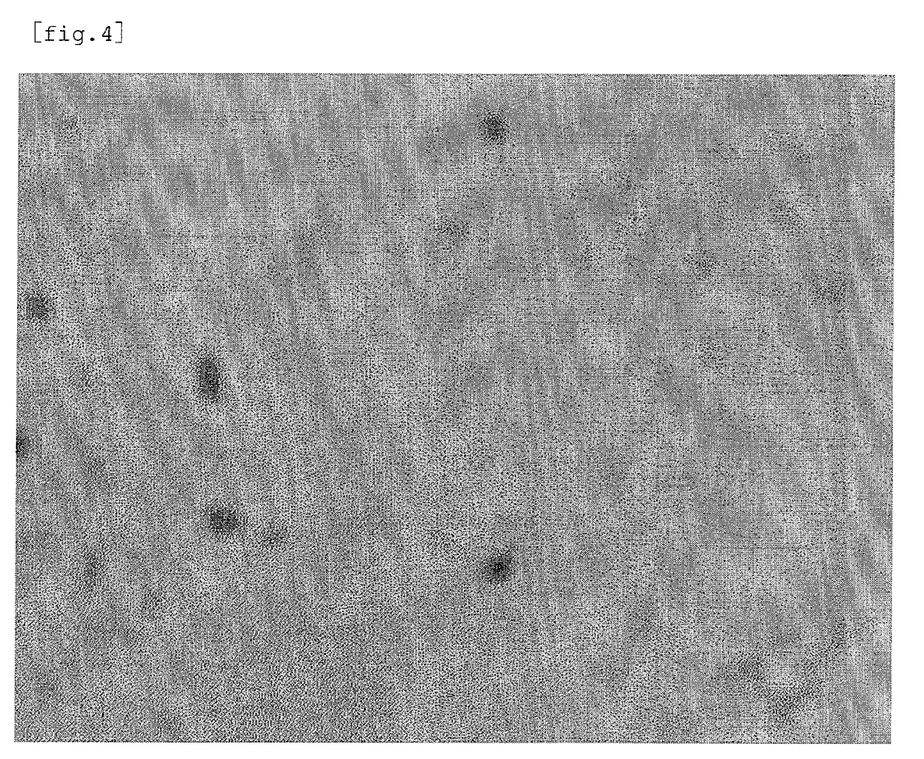
FIG. 4 is a microphotographic view of Lotion 5 of Example 5.
Figure 5:
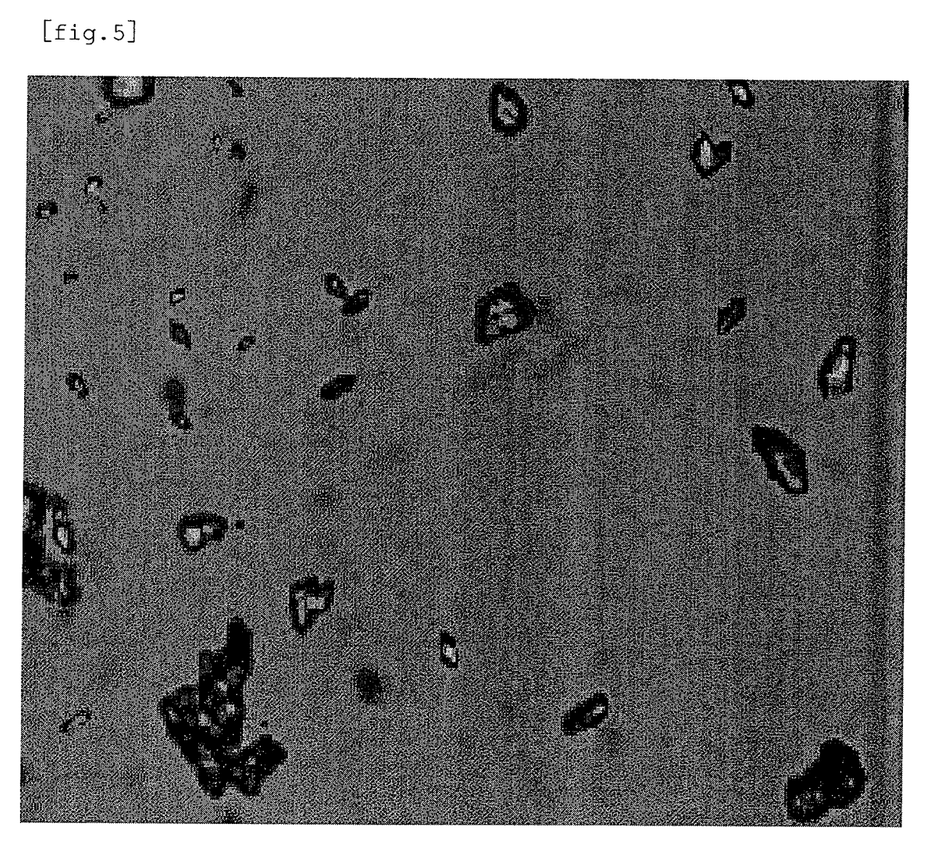
FIG. 5 is a microphotographic view of comparative Lotion 6 of Example 5.
Figure 6:
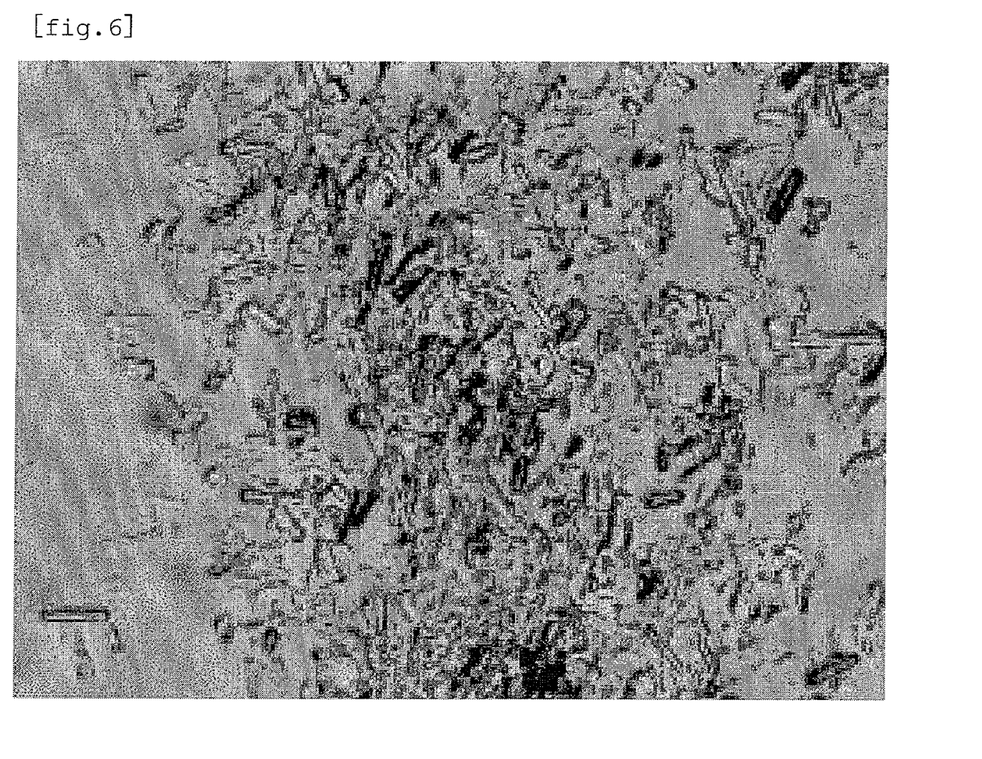
FIG. 6 is a microphotographic view of comparative Lotion 7 of Example 5.

According to Table 3 below, Lotion 5 was prepared in a manner similar to that of Example 4. In the formulation of Example 5, Comparative Lotion 6 (Comparative Example 6) in which lactic acid was replaced with ethanol and Comparative Lotion 7 (Comparative Example 7) in which lactic acid was replaced with phosphoric aid were prepared, respectively. Subsequently, each of those lotions as well as Lotion 5 were subjected to a calculation of a ratio of crystalline areas in a manner similar to that of Example 4. The results were 0% in Lotion 5, 4% in Comparative Lotion 6, and 7% in Comparative Lotion 7, respectively. FIGS. 4 to 6 show microscopic photographs of Lotion 5, Comparative Lotion 6, and Comparative Lotion 7, respectively. Here, the effects of the present invention were also recognized.

TABLE 3

| Components | % by mass |
|---|---|
| Luliconazole | 5 |
| Diisopropyl adipate | 12 |
| Lactic acid | 4 |
| Ethanol | 79 |
| Total | 100 |

Examples 6 and 7 and Comparative Example 8

According to Table 4 below, Lotion 6 (Example 6) was prepared in a manner similar to that of Example 4. In the formulation of Example 6, Lotion 7 (Example 7) in which benzyl alcohol of Lotion 6 was replaced with ethanol and Comparative Lotion 8 (Comparative Example 8) in which benzyl alcohol and lactic acid of Lotion 6 were replaced with ethanol were prepared, respectively. They were subjected to measurement of the amount of agent that has permeated through the nail in a manner similar to that of Example 4. Consequently, the amount of agent that has penetrated through the nail with respect to Lotion 6 was 6.30 when that of Lotion 7 was 1 (the amount of agent that has penetrated through the nail with respect to Lotion 6 was 58 μg per 1 cm³ of the nail, while that of Lotion 7 was 9.2 μg), while the amount of agent that has penetrated through the nail with respect to Comparative Lotion 8 was 0.61. In other words, it is found that the addition of lactic acid alone and the addition of both lactic acid and benzyl alcohol lead to 1.65- and 10.40-fold increase in penetrability of luliconazole into the nail. In consideration of those results together with those of Example 4 described above, it is found that in the pharmaceutical composition of the present invention, a penetration-accelerating agent such as benzyl alcohol exerts an original penetration-accelerating effect. Therefore, it is also found that the pharmaceutical composition of the present invention preferably contains such a component. Hereinafter, as an indicator for penetration-absorption, the amount of agent that has penetrated through the nail with respect to each sample when that of the control samples such as Lotion 7 is 1 is referred to as "penetration-absorbance ratio".

TABLE 4

| Components | % by mass |
| --- | --- |
| Luliconazole | 1 |
| Benzyl alcohol | 4 |
| Ethanol | 93.5 |
| Lactic acid | 1 |
| Polyvinyl pyrrolidone | 0.5 |
| Total | 100 |

Examples 8 to 13

According to Table 5 below, Lotions 8 to 13 containing the pharmaceutical composition of the present invention were prepared in a manner similar to that of Example 4. They were subjected to measurement of the amount of agent that has penetrated through the nail in a manner similar to that of Example 4. Consequently, the amount of agent that has penetrated through the nail (penetration-absorbance ratio) with respect to each of Lotions 8 to 13 when the amount of agent that has penetrated through the nail with respect to Lotion 7 was 1 was determined. The results are shown in Table 6. It is found that the pharmaceutical composition of the present invention preferably contains diester of dibasic acid, such as diisopropyl adipate. Any of those is known as a component for accelerating percutaneous absorption in dermal external preparations or the like. As for the penetration of luliconazole through the nail, in particular, it is found that diester of dibasic acid showed significant efficacy.

TABLE 5

| Components | % by mass |
| --- | --- |
| Luliconazole | 1 |
| Component shown in Table 6 | 10 |
| Ethanol | 87.5 |
| Lactic acid | 1 |
| Polyvinyl pyrrolidone | 0.5 |
| Total | 100 |

TABLE 6

| Sample | Component | Penetration-absorbance ratio |
| --- | --- | --- |
| Lotion 8 | Diisopropyl adipate | 9.57 |
| Lotion 9 | Trans-cinnamic acid | 1.53 |
| Lotion 10 | Propylene glycol | 1.26 |
| Lotion 11 | Eugenol | 1.11 |
| Lotion 12 | Trimethylphenol | 1.70 |
| Lotion 13 | Octyldodecanol | 2.14 |

Examples 14 and 15

According to Table 7 below, Lotion 14 containing the pharmaceutical composition of the present invention was prepared in a manner similar to that of Example 4. Simultaneously, Lotion 15, in which benzyl alcohol of Lotion 14 was replaced with ethanol, was also prepared. Subsequently, the measurement of the amount of agent that has penetrated through the nail was carried out by the method described in Example 4 to obtain the amount of agent that has penetrated through the nail (penetration-absorbance ratio) with respect to each of Lotions 14 to 15 when the amount of agent that has penetrated through the nail with respect to Lotion 7 was 1. The penetration-absorbance ratio of Lotion 14 was 14.88 and the penetration-absorbance ratio of Lotion 15 was 4.19. From the result, it is found that in the pharmaceutical composition of the present invention, luliconazole is increased in penetrability through the nail by propylene carbonate. In addition, it is also found that the addition of benzyl alcohol leads to a 3.55-fold increase in penetrability.

TABLE 7

| Components | % by mass |
| --- | --- |
| Luliconazole | 1 |
| Propylene carbonate | 10 |
| Ethanol | 83.5 |
| Benzyl alcohol | 4 |
| Lactic acid | 1 |
| Polyvinyl pyrrolidone | 0.5 |
| Total | 100 |

Examples 16 and 17

According to Table 8 below, Lotion 16 containing the pharmaceutical composition of the present invention was prepared in a manner similar to that of Example 4. Simultaneously, Lotion 17, in which N-methyl-4-pyrrolidone of Lotion 16 was replaced with ethanol, was also prepared. Subsequently, the measurement of the amount of agent that has penetrated through the nail was carried out by the method described in Example 4 to obtain the amount of agent that has penetrated through the nail (penetration-absorbance ratio) with respect to Lotion 16 when the amount of agent that has penetrated through the nail with respect to Lotion 17 was 1. The penetration-absorbance ratio of Lotion 16 was 4.12, and further acceleration of agent penetrability as compared with that of Lotion 17 in which the penetrability of agent through the nail is accelerated by a combination of benzyl alcohol, diisopropyl adipate, and lactic acid was obtained. Therefore, an excellent effect of the addition of N-methyl-2-pyrrolidone was recognized. In other words, it is found that a particularly preferable mode of the pharmaceutical composition of the present invention contains lactic acid, diester of dibasic acid, benzyl alcohol, and N-methyl-2-pyrrolidone.

TABLE 8

| Components | % by mass |
|---|---|
| Luliconazole | 5 |
| N-methyl-2-pyrrolidone | 8 |
| Ethanol | 66.5 |
| Lactic acid | 4 |
| Benzyl alcohol | 4 |
| Diisopropyl adipate | 12 |
| Polyvinyl pyrrolidone | 0.5 |
| Total | 100 |

Example 18

According to Table 9 below, Lotion 18 containing the pharmaceutical composition of the present invention was prepared in a manner similar to that of Example 4. The measurement of the amount of agent that has penetrated through the nail was carried out by the method described in Example 4 to obtain the amount of agent that has penetrated through the nail (penetration-absorbance ratio) with respect to Lotion 18 when the amount of agent that has penetrated through the nail with respect to Lotion 7 was 1, resulting in a penetration-absorbance ratio of 3.03. It is found that the pharmaceutical composition of the present invention has an excellent penetration-accelerating action. Even in the absence of benzyl alcohol, a combination of N-methyl-2-pyrrolidone and diisopropyl adipate allows an increase in permeability through the nail.

TABLE 9

| Components | % by mass |
|---|---|
| Luliconazole | 1 |
| N-methyl-2-pyrrolidone | 8 |
| Diisopropyl adipate | 10 |
| Ethanol | 76.5 |
| Lactic acid | 4 |
| Polyvinyl pyrrolidone | 0.5 |
| Total | 100 |

Example 19

According to Table 10 below, Lotion 19 containing the pharmaceutical composition of the present invention was prepared in a manner similar to that of Example 4. The measurement of the amount of agent that has penetrated through the nail was carried out by the method described in Example 4 to obtain the amount of agent that has penetrated through the nail (penetration-absorbance ratio) with respect to Lotion 19 when the amount of agent that has penetrated through the nail with respect to Lotion 7 was 1, resulting in a penetration-absorbance ratio of 2.49. It is found that the pharmaceutical composition of the present invention has an excellent penetration-accelerating action. Even in the absence of N-methyl-2-pyrrolidone, a combination of benzyl alcohol and diisopropyl adipate allows an increase in penetrability through the nail.

TABLE 10

| Components | % by mass |
|---|---|
| Luliconazole | 1 |
| Benzyl alcohol | 5 |
| Diisopropyl adipate | 10 |
| Ethanol | 79.5 |
| Lactic acid | 4 |
| Polyvinyl pyrrolidone | 0.5 |
| Total | 100 |

Example 20

According to Table 11 below, Lotion 20 containing the pharmaceutical composition of the present invention was prepared in a manner similar to that of Example 4. The measurement of the amount of agent that has penetrated through the nail was carried out by the method described in Example 4 to obtain the amount of agent that has penetrated through the nail (penetration-absorbance ratio) with respect to Lotion 20 when the amount of agent that has penetrated through the nail with respect to Lotion 7 was 1, resulting in a penetration-absorbance ratio of 2.49. It is found that the pharmaceutical composition of the present invention has an excellent penetration-accelerating action. This result indicates that diisopropyl adipate can be replaced with diethyl sebacate and the result of diisopropyl adipate can be applied to generally all of dibasic acid diesters.

TABLE 11

| Components | % by mass |
|---|---|
| Luliconazole | 1 |
| Benzyl alcohol | 5 |
| Diethyl sebacate | 10 |
| Ethanol | 79.5 |
| Lactic acid | 4 |
| Polyvinyl pyrrolidone | 0.5 |
| Total | 100 |

Example 21

According to Table 12 below, Lotion 21 containing the pharmaceutical composition of the present invention was prepared in a manner similar to that of Example 4. The measurement of the amount of agent that has penetrated through the nail was carried out by the method described in Example 4 to obtain the amount of agent that has penetrated through the nail (penetration-absorbance ratio) with respect to Lotion 21 when the amount of agent that has penetrated through the nail with respect to Lotion 7 was 1, resulting in a penetration-absorbance ratio of 2.34. It is found that the pharmaceutical composition of the present invention has an excellent penetration-accelerating action. In the pharmaceutical composition of the present invention, it can be seen that the penetration-accelerating effect by the solvent appears clearly.

TABLE 12

| Components | % by mass |
|---|---|
| Luliconazole | 1 |
| Benzyl alcohol | 5 |
| Triacetin | 10 |
| Ethanol | 79.5 |

TABLE 12-continued

| Components | % by mass |
|---|---|
| Lactic acid | 4 |
| Polyvinyl pyrrolidone | 0.5 |
| Total | 100 |

Example 22

According to Table 13 below, Lotion 22 containing the pharmaceutical composition of the present invention was prepared in a manner similar to that of Example 4. The measurement of the amount of agent that has penetrated through the nail was carried out by the method described in Example 4 to obtain the amount of agent that has penetrated through the nail (penetration-absorbance ratio) with respect to Lotion 22 when the amount of agent that has penetrated through the nail with respect to Lotion 7 was 1, resulting in a penetration-absorbance ratio of 2.05. It is found that the pharmaceutical composition of the present invention has an excellent penetration-accelerating action. In the pharmaceutical composition of the present invention, it can be seen that the penetration-accelerating effect by the solvent appears clearly.

TABLE 13

| Components | % by mass |
|---|---|
| Luliconazole | 1 |
| Benzyl alcohol | 5 |
| Triethyl citrate | 10 |
| Ethanol | 79.5 |
| Lactic acid | 4 |
| Polyvinyl pyrrolidone | 0.5 |
| Total | 100 |

Example 23

According to Table 14 below, Lotion 23 containing the pharmaceutical composition of the present invention was prepared in a manner similar to that of Example 4. The measurement of the amount of agent that has penetrated through the nail was carried out by the method described in Example 4 to obtain the amount of agent that has penetrated through the nail (penetration-absorbance ratio) with respect to Lotion 23 when the amount of agent that has penetrated through the nail with respect to Lotion 7 was 1, resulting in a penetration-absorbance ratio of 1.68. It is found that the pharmaceutical composition of the present invention has an excellent penetration-accelerating action. In the pharmaceutical composition of the present invention, it can be seen that the penetration-accelerating effect by the solvent appears clearly.

TABLE 14

| Components | % by mass |
|---|---|
| Luliconazole | 1 |
| Benzyl alcohol | 5 |
| Butyl acetate | 10 |
| Ethanol | 79.5 |
| Lactic acid | 4 |
| Polyvinyl pyrrolidone | 0.5 |
| Total | 100 |

Example 24

According to Table 15 below, Lotion 24 containing the pharmaceutical composition of the present invention was prepared in a manner similar to that of Example 4. The measurement of the amount of agent that has penetrated through the nail was carried out by the method described in Example 4 to obtain the amount of agent that has penetrated through the nail with respect to Lotion 24, resulting in 260.3 µg/cm$^3$. It is found that the pharmaceutical composition of the present invention has an excellent penetration-accelerating action.

TABLE 15

| Components | % by mass |
|---|---|
| Luliconazole | 1 |
| N-methyl-2-pyrrolidone | 8 |
| Benzyl alcohol | 4 |
| Diisopropyl adipate | 10 |
| Ethanol | 72.5 |
| Lactic acid | 4 |
| Polyvinyl pyrrolidone | 0.5 |
| Total | 100 |

INDUSTRIAL APPLICABILITY

According to the present invention, it becomes possible to provide a pharmaceutical composition for external use having an excellent penetration-absorption of luliconazole and/or a salt thereof.

What is claimed is:

1. A pharmaceutical composition for external use, comprising:
   (i) luliconazole represented by the following structural formula (1) and/or a salt thereof, wherein the composition comprises luliconazole in an amount of 0.5 to 15% by mass; and
   (ii) 1-10% by mass lactic acid and/or a salt thereof; and
   (iii) ethanol, wherein the concentration of ethanol is 50-90% by mass Structural formula (1)

[Chem 1]

2. A pharmaceutical composition for external use according to claim 1, wherein the ratio of lactic acid to luliconazole is 0.1 to 10.

3. A pharmaceutical composition for external use according to claim 2, wherein the ratio of lactic acid to luliconazole is 0.5 to 5.

4. A pharmaceutical composition for external use according to claim 3, wherein the ratio of lactic acid to luliconazole is 0.8 to 2.

* * * * *